(12) United States Patent  
Pozos et al.

(10) Patent No.: US 6,673,026 B2
(45) Date of Patent: Jan. 6, 2004

(54) FORCE MEASURING DEVICE AND METHOD

(75) Inventors: Robert S. Pozos, San Diego, CA (US); Jose L. Agraz, La Jolla, CA (US)

(73) Assignee: San Diego State University Foundation, San Diego, CA (US)

( * ) Notice: Subject to any disclaimer, the term of this patent is extended or adjusted under 35 U.S.C. 154(b) by 201 days.

(21) Appl. No.: 09/819,183

(22) Filed: Mar. 27, 2001

(65) Prior Publication Data

US 2001/0049482 A1 Dec. 6, 2001

Related U.S. Application Data

(63) Continuation-in-part of application No. 09/536,834, filed on Mar. 27, 2000, now Pat. No. 6,352,516.

(51) Int. Cl.$^7$ ............................................... A61B 5/103
(52) U.S. Cl. ....................................................... 600/587
(58) Field of Search ................................ 600/300, 301, 600/587, 588, 589, 590, 591, 592, 593, 594, 595; 434/247; 482/2–4, 51–111; 463/1–47

(56) References Cited

U.S. PATENT DOCUMENTS

| | | | |
|---|---|---|---|
| 4,512,567 A | 4/1985 | Phillips ........................ 272/73 |
| 4,702,108 A | 10/1987 | Amundsen et al. ............ 73/379 |
| 4,751,642 A | 6/1988 | Silva et al. ................. 364/413 |
| 5,001,632 A | 3/1991 | Hall-Tipping .......... 364/413.04 |
| 5,085,226 A | 2/1992 | DeLuca et al. ............. 128/733 |
| 5,301,683 A | 4/1994 | Durkan ........................ 128/744 |
| 5,377,100 A | 12/1994 | Pope et al. .................. 364/410 |
| 5,462,065 A | 10/1995 | Cusimano ................... 128/782 |
| 5,579,238 A | 11/1996 | Krugman .................... 364/508 |
| 5,713,370 A | 2/1998 | Cook .......................... 128/774 |
| 5,745,376 A | 4/1998 | Barker et al. ............... 364/508 |
| 5,885,231 A | 3/1999 | Cramer et al. .............. 600/595 |
| 5,899,616 A | 5/1999 | Caplan ........................ 400/489 |
| 5,957,813 A | 9/1999 | Macdonald .................... 482/44 |
| 5,964,719 A | 10/1999 | Costello et al. ............. 600/595 |
| 6,162,189 A | 12/2000 | Girone et al. ............... 600/592 |
| 6,259,382 B1 | 7/2001 | Rosenberg ................... 341/20 |
| 6,264,621 B1 * | 7/2001 | Paske ......................... 600/587 |

* cited by examiner

Primary Examiner—Max F. Hindenburg
Assistant Examiner—Pamela Wingood
(74) Attorney, Agent, or Firm—Pennie & Edmonds LLP

(57) ABSTRACT

The present invention relates to a device and method for measuring force, primarily due to fatigue. In one embodiment, a finger fatigue measuring system is provided which measures the force output from fingers while the fingers are repetitively generating forces as they strike a keyboard. Force profiles of the fingers are generated from the measurements and evaluated for fatigue. The system can be used clinically to evaluate patients, to ascertain the effectiveness of clinical intervention, pre-employment screening, to assist in minimizing the incidence of repetitive stress injuries at the keyboard, mouse, joystick, and to monitor effectiveness of various finger strengthening systems. The system can also be used in a variety of different applications adapted for measuring forces produced during performance of repetitive motions.

28 Claims, 17 Drawing Sheets

FORCE MEASURING DEVICE AND METHOD

CROSS-REFERENCE TO RELATED APPLICATIONS

This application is a continuation-in-part of U.S. Ser. No. 09/536,834, which was filed on Mar. 27, 2000, and which issued as U.S. Pat. No. 6,352,516 on Mar. 5, 2002.

BACKGROUND OF THE INVENTION

1. Field of the Invention

The invention relates generally to a device and method for measuring force, primarily as a function of fatigue, and more particularly to a device and method for monitoring a specific body part of a person for fatigue by measuring and evaluating the forces generated by that body part as it performs a series of sequential or repetitive motions.

2. Description of the Related Art

The prior art discloses various techniques for monitoring fatigue. Generally, a single muscle or a related group of muscles is monitored for fatigue. In Eskelinen, U.S. Pat. No. 5,349,963, for example, the fatigue level of a particular muscle is determined from electromyographic (EMG) signals that are measured from that muscle.

EMG signals may be employed to detect muscle fatigue while the muscle undergoes isometric- or isotonic-type testing. For isometric-type testing, electrodes are attached to a muscle being studied and the test subject is instructed to apply a constant force with that muscle while maintaining that muscle in a static position. For isotonic-type testing, electrodes are attached to a muscle being studied and the test subject is instructed to perform multiple cycles of repetitive motions with that muscle. In both types of testing, EMG signals, which are measurements of muscle output activity, are collected for fatigue analysis.

The prior art also discloses force measuring systems that measure the amount of force generated by a muscle or group of muscles. For example, in Krugman, U.S. Pat. No. 5,579,238 and Barker et al., U.S. Pat. No. 5,745,376, the force that a user applies to a keyboard is measured. Feedback is provided to the user when excessive force is detected so that the user can reduce the force applied to the keyboard and thereby reduce the likelihood of developing repetitive stress injuries (RSI).

In Krugman, finger force is measured by way of a vibration detecting device attached to the keyboard. The signals from the vibration sensor are proportional to the force produced by the fingers. The force data is used to trigger auditory warning signals if the force exceeds a certain threshold level. In Barker et al., an initial force is compared with a secondary force. If the secondary force is larger than the initial force, the system triggers an auditory warning signal.

The present invention differs from the teachings of Krugman and Barker, in that both of these patents relate to the detection of excessive force, whereas the present invention relates primarily to the detection of decreased force characteristic of fatigue.

In U.S. Pat. No. 5,855,231, measurement of force is used to study motor deficit for the purpose of diagnosis and treatment monitoring. However, force measurements and data processing are not optimized for monitoring fatigue. In addition, analog signal processing requires amplification and conversion.

Because of the importance of avoiding muscle fatigue, there is a general need to provide techniques and systems for monitoring the onset of fatigue. The present invention relates to such techniques and systems, which are based on evaluating the force profiles of a muscle or group of muscles. In addition to being useful for monitoring fatigue, such techniques and systems are also useful for a variety of other applications a described herein.

SUMMARY OF THE INVENTION

Repetitive Stress Injury (RSI) is a general term that describes the consequences of repetitive activity, usually of the fingers, wrist, elbow or shoulder resulting in numbness, pain and an inability to work productively. The basic assumption for the pathogenesis of RSI is that muscles, which are doing repetitive work, will continue to generate force even after they become fatigued. Damage occurs when the muscles are not properly rested. Thus, the prime time to protect persons from RSI is during the time when the muscles are becoming fatigued.

Fatigue is usually manifested as a decrease in the amount of force produced over time. Most subjects who are undergoing repetitive motion during exercise (e.g. curls, leg exercises) will generate sufficient force to continue their exercise until they fatigue, after which there is a decrease in the amount of force being generated. However, in some subjects, as the muscles become fatigued, the force will increase temporarily and then decrease. In those situations, the subject responds to fatigue by changing the exercise rate, and/or other muscles are involuntarily recruited to assist the fatigued muscles. In any event, the object of the present invention is to avoid fatigue.

Subjects who have RSI are not able to generate as much force as non-afflicted subjects, nor are they able to conduct an exercise for as long a period of time. However, the degree of impairment is usually not quantifiable. Thus, the clinician is left with only subjective impressions about the improvement of the patient after surgical/clinical intervention. In a preferred embodiment, the invention provides an apparatus that can evaluate the force generated by the fingers as they perform repetitive motions. The same apparatus can be used to evaluate both impaired and normal subjects.

Because of the importance of avoiding muscle fatigue, there is a general need to provide techniques and systems for monitoring the onset of fatigue. The present invention relates to such techniques and systems, which are based on evaluating the force profiles of a muscle or group of muscles. In addition to being useful for monitoring fatigue, such techniques and systems are also useful for a variety of other applications as described herein.

The invention may further provide a keyboard (regular or ergonomic) as the housing for the force sensing member of the combined hardware/software system. The combined hardware/software system may also include a mouse, a joystick, or any other force sensing member, having finger-(or hand-) actuated keys or buttons. It should be understood that as used herein, the term "keys or buttons" contemplates other apparatus configurations as well, such as levers, switches, knobs, etc. When these force sensing members are included, the invention serves as an active fatigue monitor that evaluates the condition of the user from the force profiles and alerts the user to rest when it determines the user has become fatigued.

The FMS is capable of quantifying finger fatigue recorded in real-time during repetitive motion of the fingers, either separately or together. In some regards, the FMS is like to a treadmill for fingers. It can be used clinically to evaluate patients, to ascertain the effectiveness of clinical intervention, pre-employment screening, to assist in minimizing the incidence of RSI at the keyboard, mouse, joystick, and to monitor effectiveness of various finger strengthening systems. In preferred applications, the key output measure is the force produced by the fingers. The conventional treadmill allows for a specific amount of work to be done until the person tires. Simultaneously, the person's heart rate can be monitored. The FMS is similar in that it allows the user or the clinician to ascertain the amount of time a person can maintain a given force while conducting repetitive finger movements. During this time, EMG signals may also be collected by the FMS and recorded from muscles in a manner similar to the recording of heart rate while using a conventional treadmill.

In addition, once a clinical intervention has occurred, the onset of fatigue should be increased over that of the pre-treatment condition. The FMS allows the clinician to be more objective in terms of assessing the improvement of the patient.

The FMS solves the problem of the lack of quantification of finger fatigue for subjects with various pathologies that influence their finger movements. Whether it is musicians, computer users, or any other persons applying force (repetitively or sequentially) with their fingers, the FMS allows a more scientific approach toward the management of RSI. At present, all repetitive stress injuries are considered similar. By using the FMS, it is possible to begin to discriminate between various clinical RSI manifestations.

Accordingly, the present invention relates to a method of monitoring fatigue in at least one body part of a subject performing repetitive motions, said motions including applying force to a force sensing member connected to a force measuring apparatus, said method comprising the steps of: measuring signal as a function of force produced by the body part during performance of the repetitive motions; measuring signal as a function of force effects on the force sensing member during performance of the repetitive motions; converting the signal characteristic of force production to a force production profile, and converting the signal characteristic of the effects of the force to a force effect profile.

In another embodiment of the present invention, a force sensing member is provided which is adapted for use in a force measuring apparatus for monitoring fatigue in at least one body part of a person performing repetitive motions, said force sensing member comprising: a) a force sensor functionally associated with the force sensing member that generates signal characteristic of force produced by the body part and transmitted to the input device during performance of the repetitive motions; and b) a switch sensor functionally associated with the force sensing member that generates signals when depression and release of the force sensing member occurs during performance of the repetitive motions.

In yet another embodiment of the present invention, a computer game system is provided which is adapted for monitoring a repetitive motion of at least one body part of a person playing the computer game, wherein said system comprises a force sensing member further comprising: a) a force sensor functionally associated with the force sensing member that generates signal as a function of force produced by the body part and transmitted to the force sensing member during play of the game; and b) a switch sensor functionally associated with the force sensing member that generates signal when depression and release of the force sensing member occurs during play of the game.

A further embodiment of the present invention is a method of measuring force production in at least one body part of a subject performing repetitive motions, said motions including applying force to a force sensing member connected to a force measuring apparatus, said method comprising: a) measuring digital signal as a function of force effects on the force sensing member during performance of the repetitive motions; and b) converting the signal to a force effect profile, wherein said force effect profile reflects frequency and overlap of said repetitive motions.

Additional objects, features and advantages of the invention are set forth in the claims and the detailed description of preferred embodiments which follow.

BRIEF DESCRIPTION OF THE DRAWINGS

The invention is described in detail herein with reference to the drawings in which:

FIG. 2 represents sample EMG outputs of a subject performing repetitive motions.

The accompanying drawings, which are incorporated in and constitute a part of the specification, illustrate presently preferred exemplary embodiments of the invention, and, together with the general description given above and the detailed description of the preferred embodiments given below, serve to explain the principles of the invention.

DETAILED DESCRIPTION OF THE PREFERRED EMBODIMENTS

In the workplace as well as at home, the ubiquitous nature of the computer and other "ergostressors" requires that there be apparatuses available to indicate when rest is required to prevent physical injury.

Repetitive stress injury (RSI) is a major problem facing clinicians and our society. Carpal Tunnel Syndrome (CTS), which is one form of RSI, is a significant health problem in the workplace today. The U.S. Department of Labor has concluded that CTS is the "chief occupational hazard of the 90's-disabling workers in epidemic proportions." As our society gets older, the incidence of RSI will increase. In addition, as we urge all children to become computer literate, RSI will become a major problem with our youth. By the year 2000, 30 million children will have computers at home and 40 million will have computer time at their schools.

An apparatus that can quantify the degree of impairment of subjects suffering from CTS would be useful in the medical field. The most practical non-invasive method is to evaluate the fatigability of the fingers while conducting a standard repetitive task. (As used herein, the term "repetitive" refers to both the same motion produced by the same body part, or the same motion produced by different body parts in sequence. For example, it refers both to tapping the same finger repeatedly and also to tapping all four fingers sequentially.) Such a method would be useful to hand surgeons, and physical and occupational therapists to evaluate patients suffering from RSI before and after clinical interventions. Presently, surgical intervention is used to minimize CTS. However, if the patient begins to repeat the same behavior that produced the problem, then the person may develop CTS again.

The present invention provides a force measuring system (FMS) that is useful for evaluating fatigue. When adapted for the evaluations of repetitive finger motions, it can be used to detect, avoid, and/or treat CTS.

Figure 1:
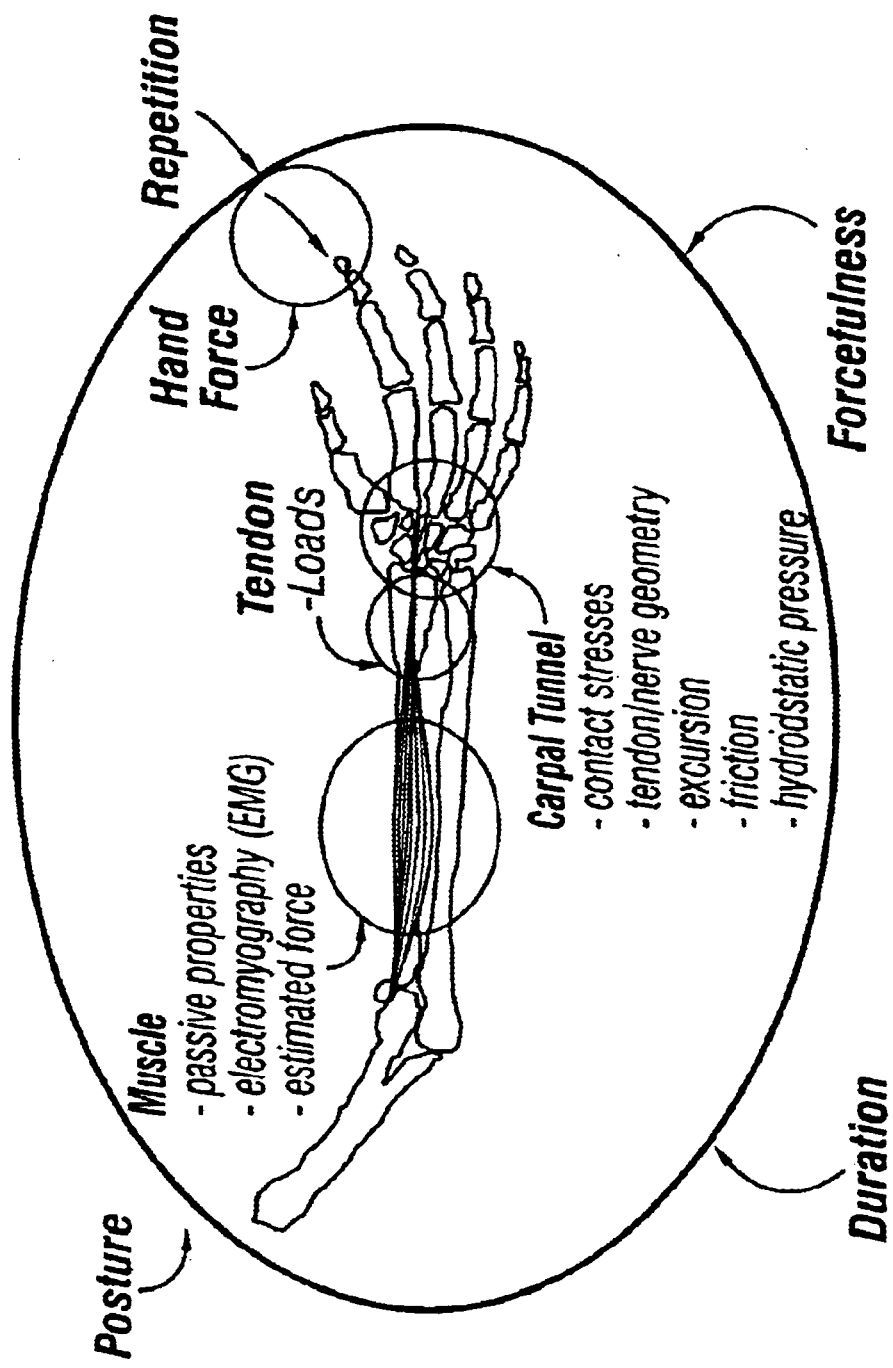
FIG. 1 is a schematic diagram illustrating the basic elements of a person's arm that work together to generate finger forces.

When studying repetitive activities involving fingers, many factors may influence the generation of finger force, such as the activity of the muscles and the tendons shown FIG. 1, but the end result of finger activation is force produced by the fingers.

Figure 2A:
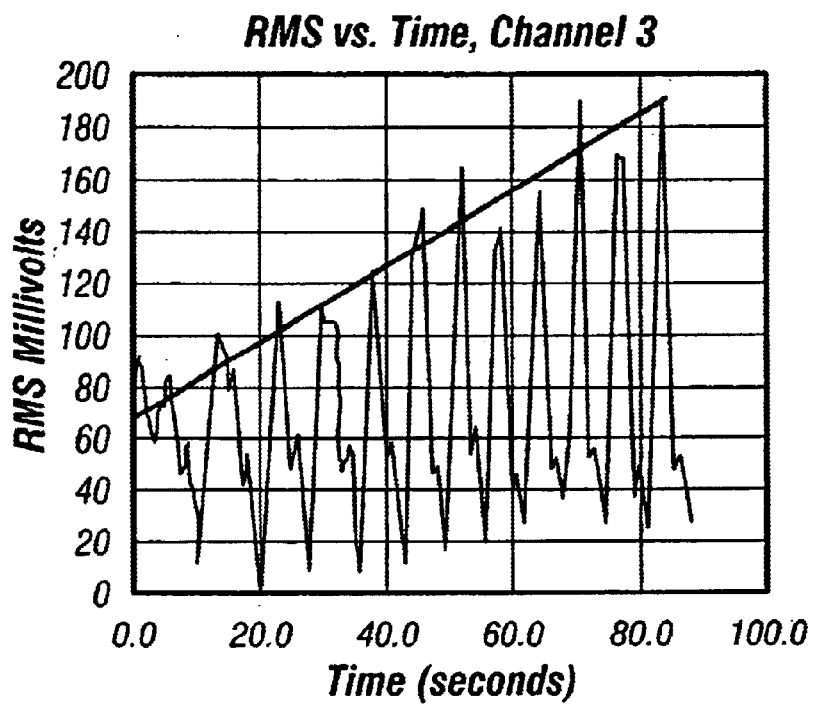
FIG. 2A depicts the relationship between EMG signal (RMS) and time.
Figure 2B:
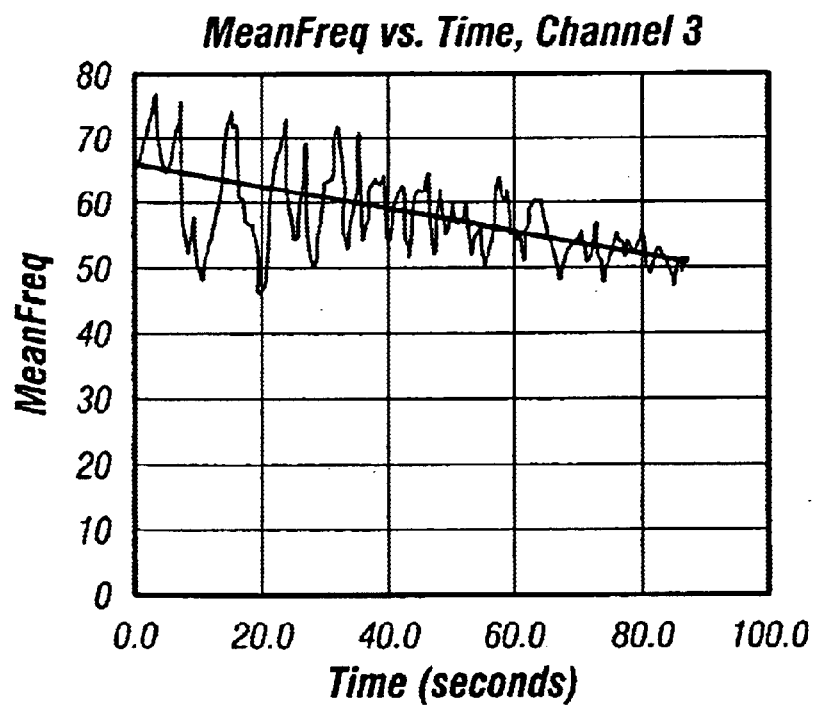
FIG. 2B depicts the relationship of EMG signal amplitude/frequency and time.

As a person fatigues while performing repetitive finger motions, EMG signal amplitude from the muscles (which can be measured in terms of root mean square (RMS)), tends to increase while the time it takes to perform the motion tends to decrease. See FIG. 2A. In addition, as the amplitude of the EMG signals increase, the frequency of the EMG signals decrease. See FIG. 2B. These EMG signal changes can be evaluated simultaneously with force measurements to enhance the ability to obtain useful clinical information from the FMS.

Figure 3A:
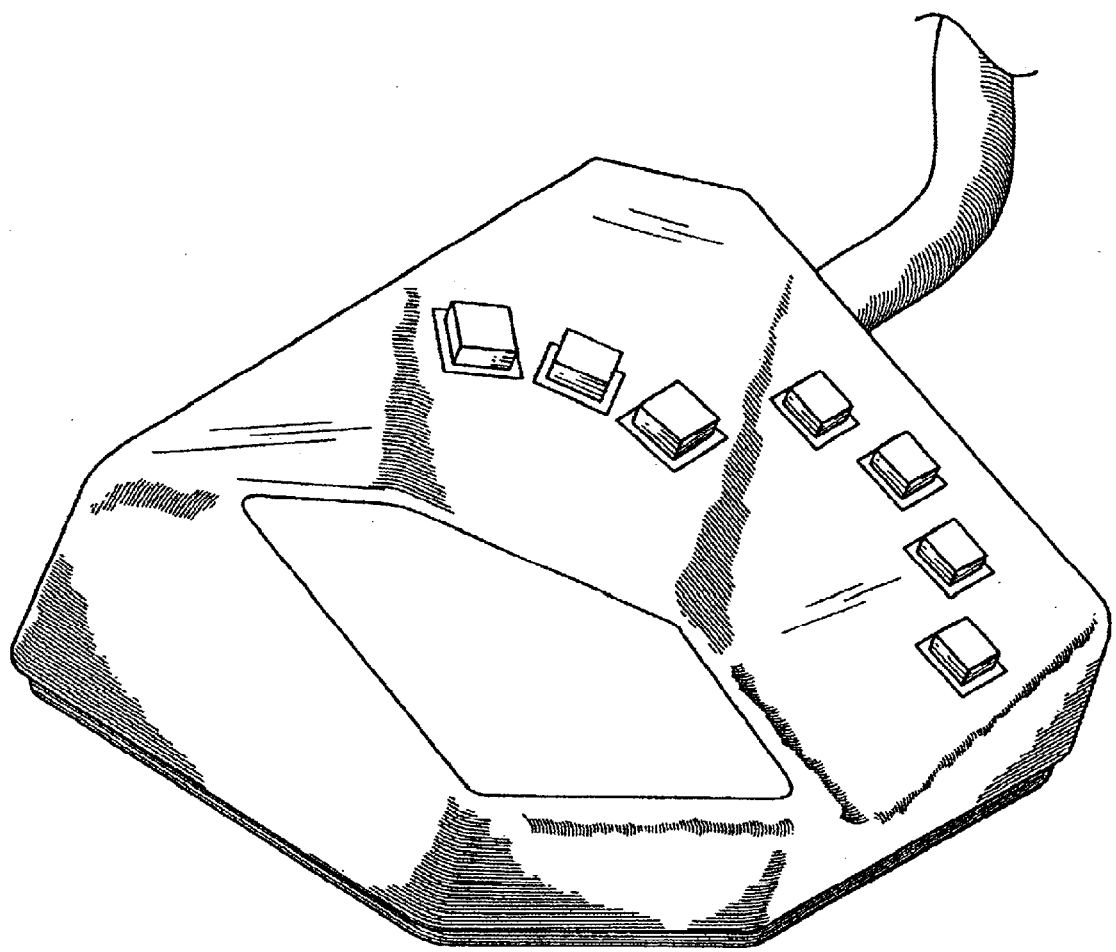
FIG. 3A, is an illustration of an ergonomic keyboard for the left hand for generating finger force profiles that are used to monitor fatigue using an FMS.

The FMS according to one embodiment of the invention is illustrated in FIG. 3A. It shows an ergonomic keyboard 10 including a housing 15 on top of which are provided a receptacle 20 for the base part of a person's left hand, and a plurality of keys 31–37. One of keys 31–33 are provided for activation by the person's thumb, key 34 for activation by the person's index finger, key 35 for activation by the person's middle finger, key 36 for activation by the person's ring finger, and key 37 for activation by the person's little finger. The person may choose any one of keys 31–33 for activation by his or her thumb. Multiple keys 31–33 are provided for the thumb to account for differing hand sizes.

Figure 3B:
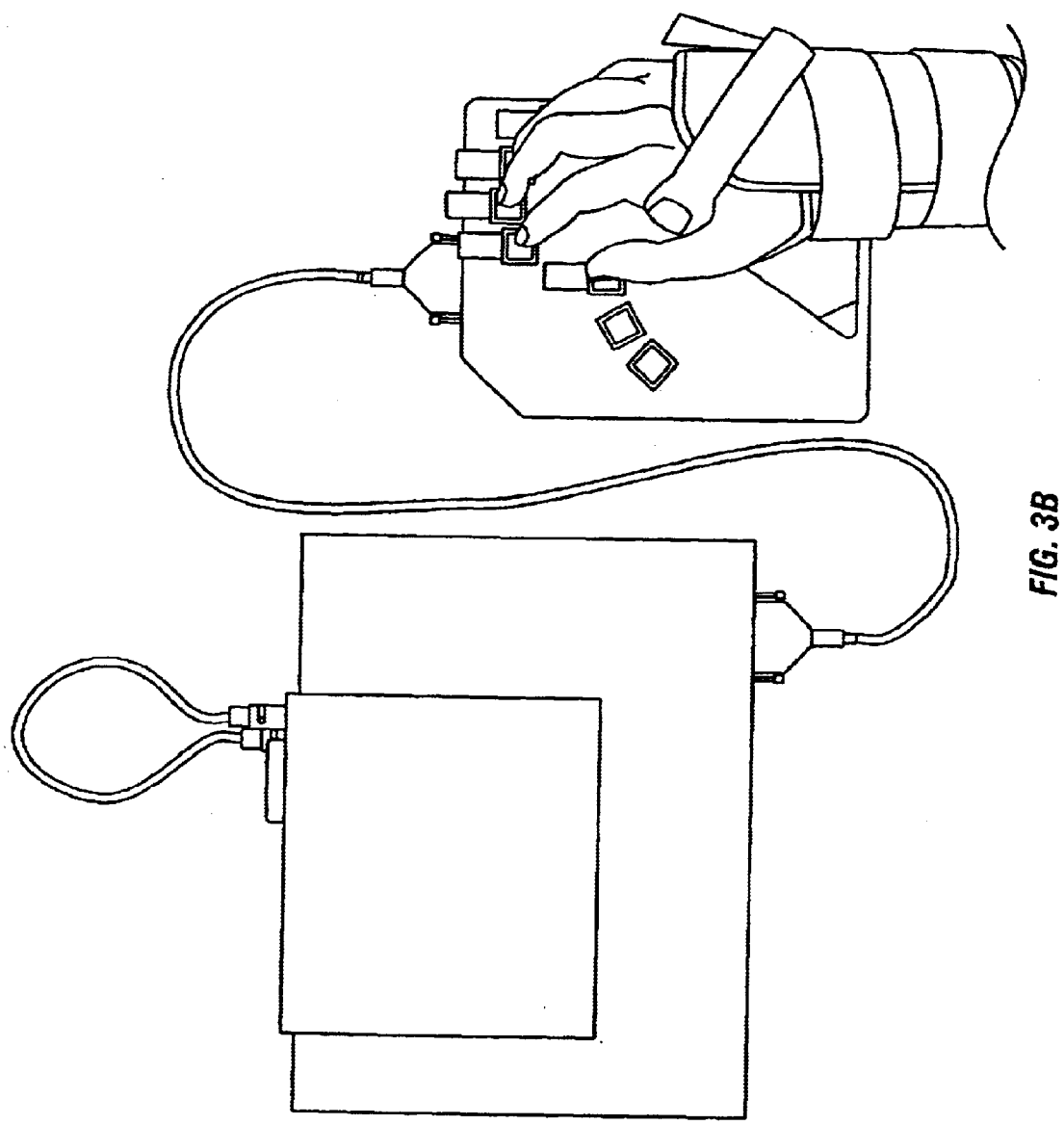
FIG. 3B is an illustration of a force measuring system for fingers, including an ergonomic keyboard for the right hand, for generating finger force profiles that are used to monitor fatigue.

The FMS illustrated in FIG. 3A evaluates the fingers of the subject's left hand. FIG. 3B illustrates an FMS that evaluates the fingers of the subject's right hand. FIG. 3B also illustrates how the person's right hand is held down in a substantially fixed position by a wrist strap 38 that is attached to the keyboard 10, so that the finger forces are generated substantially by the muscles for moving the fingers over the entire duration of the test. FIG. 3B also illustrates a signal conditioning unit 60 connected to the keyboard 10 by a cable and a power supply unit 65 for the signal conditioning unit 60 connected to an AC outlet (not shown).

Figure 4:
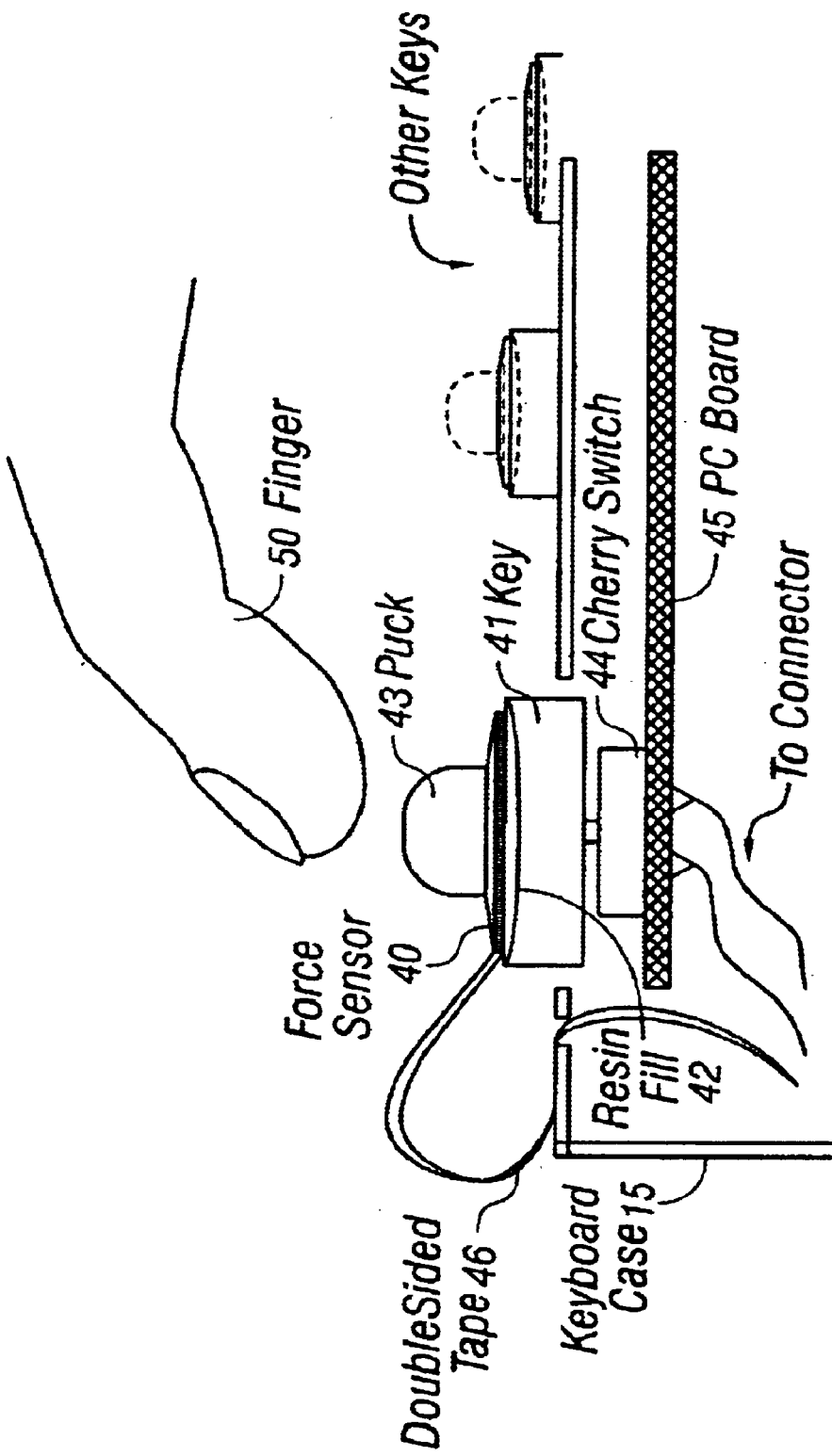
FIG. 4 is a detailed illustration of one of the keys on the ergonomic keyboard of FIG. 3A.

Each of the keys 31–37 of the apparatus depicted in FIG. 3A is "functionally associated" with a force transducer or "force sensor" and a "switch sensor." As used herein, the term "functionally associated" refers to any means of coupling the action of the keys or buttons (i.e. the force sensing members) to the production of signals that can be detected by the force sensor and the switch sensor. Different types of digital or analog force sensors can be used, such as a Flexiforce™ sensor (Telescan, Inc., South Boston, Mass.). FIG. 4 is a more detailed illustration of a representative one of the keys 31–37, and shows a force sensor 40. The sensor 40 is supported on a key cap 41 through a resin 42. The resin 42 fills a concave space formed on an upper surface of the key cap 41. The finger force is applied by a person's finger 50 and transmitted through a puck 43, which is preferably plastic, to the key cap 41 to actuate the switch sensor, which is sometimes referred to as "cherry switch", 44. The actuation state (i.e. depressed or released) of the cherry switch 44 is transmitted to a data acquisition card 70 (see FIG. 5) over a PC board 45. The force sensor and switch sensor signals are transmitted to the data acquisition card 70 over a cable, which is held onto the housing or case 15 using a double-sided tape 46.

In one embodiment of the present invention an apparatus such as the one depicted in FIG. 3A is adopted for use as a "training device" to help a user develop the stamina to avoid fatigue. Such an apparatus may have keys with adjustable spacing and resistance. When a subject uses the apparatus over an extended period of time as part of a training program, the onset of fatigue may be observed to occur later and later. By increasing the resistance and decreasing the spacing between the keys during this training program, the beneficial effects of the training program may be further optimized.

In another embodiment of the invention, the apparatus is adapted to measure both the characteristics of the force being applied to the keys via the force sensors, and also the location of the keys (i.e. depressed or released) during application of the force via the key switches, or "switch sensors". Whereas the former allows for measurement of changes in force production which is used to generate a "force production profile," the latter allows for measurement of changes in the timing of key depression and release which is used to generate a "force effect profile" (i.e. force production and force effect).

Although in one embodiment of the invention both force profiles are generated and analyzed, in an alternative embodiment, only one is recorded and analyzed. In either, a change or "trend" in the profile over time serves as an indicator of the onset of fatigue.

In an alternate embodiment of the FMS depicted in FIG. 3A and illustrated in FIG. 4, a force sensor like the one used for the key switches 44 is provided underneath the receptacle 20 for the base part of the hand. As with the force sensors 40 used with the key switches 44, the force sensor for the receptacle measures the force generated by the base of the hand and transmits signals to the signal conditioning unit 60, in particular the analog signal conditioning unit 62, for processing. The forces generated by the base of the hand may be used as another measurement of fatigue, since as the subject becomes fatigued using the fingers, more force will be applied by the base of the hand.

Figure 5:
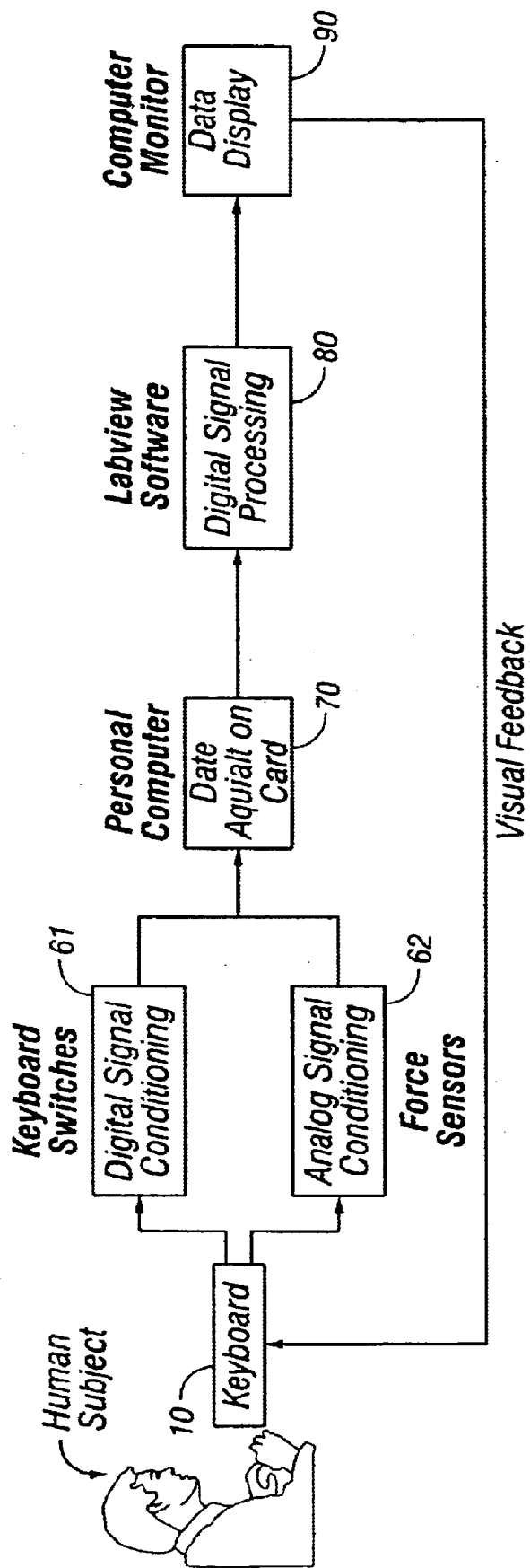
FIG. 5 is a block diagram of a combined force measuring system, including hardware, software and a keyboard, for monitoring the onset of finger fatigue.

FIG. 5 is a block diagram of the overall system including the ergonomic keyboard 10, a digital signal conditioning circuit 61 for the keyboard switches, an analog signal conditioning circuit 62 for the force sensors, a data acquisition card 70, a digital signal processing unit 80, and a data display 90. The signal conditioning unit 60 shown in FIG. 3B includes both the digital signal conditioning circuit 61 and the analog signal conditioning circuit 62. In the exemplary embodiment, the data acquisition card 70 is installed in a personal computer and the data display 90 constitutes the display unit of the personal computer. Further, the digital signal processing unit 80 comprises a microprocessor for the personal computer executing a series of program steps to store the acquired data in a memory and to retrieve and process the data for graphic representation through the data display 90.

As shown in FIG. 5, both the keyboard switches and force sensors supply signal to the data acquisition card. In the embodiment as shown, mixed analog and digital signals are transmitted to the data acquisition card (70). However, in an alternate embodiment (not shown), both the keyboard switches and force sensors transmit digital signals to the data acquisition card (70), thereby eliminating the need to amplify the analog signal and convert the amplified analog signal to digital signal for further processing and evaluation.

Figure 6:
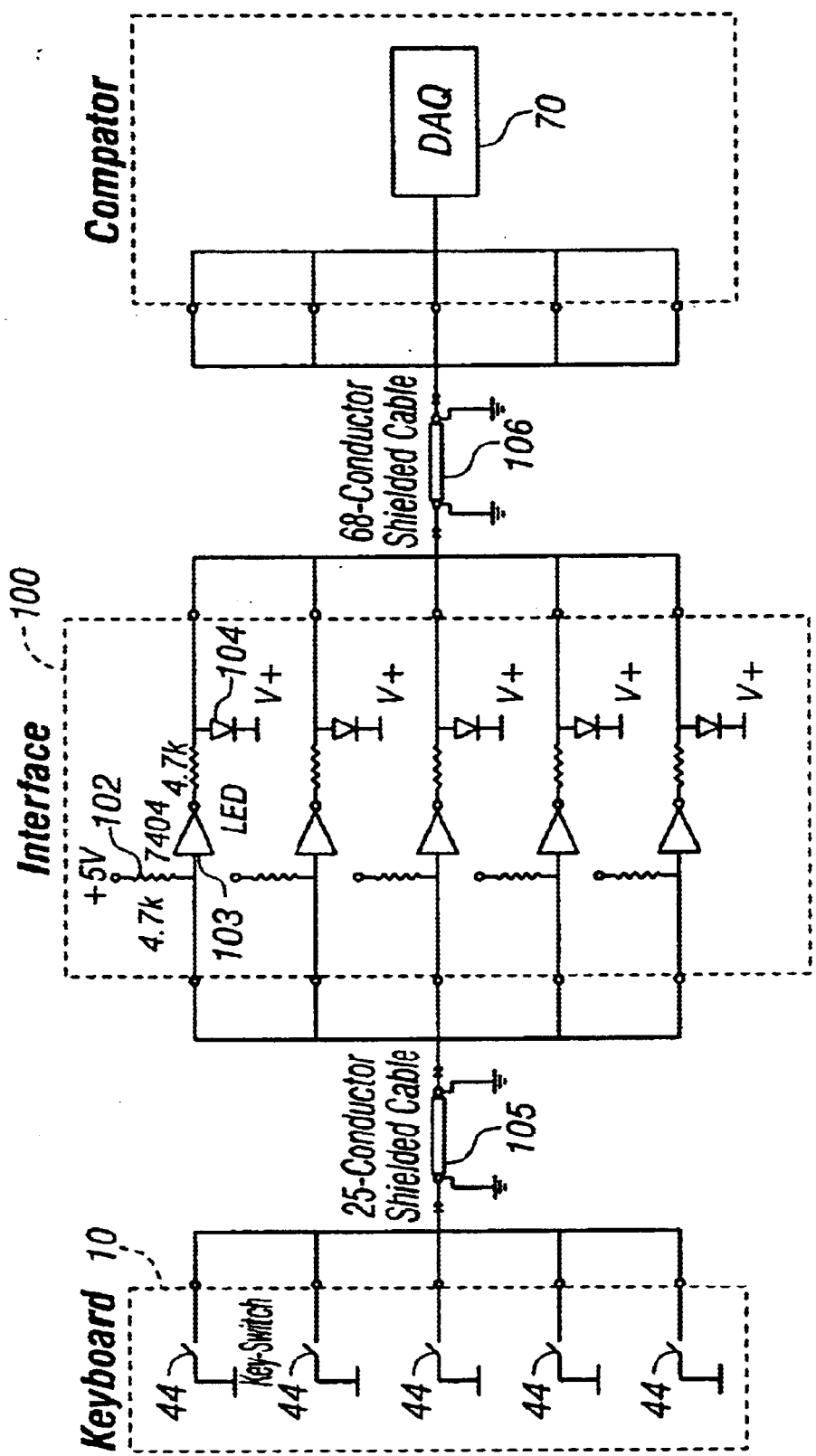
FIG. 6 is a schematic illustration of a digital signal processing circuit for the keyboard switches arranged on the ergonomic keyboard of FIG. 3A.

Referring to FIG. 6, the digital signal conditioning circuit 61 for the keyboard switches 44 comprises an interface 100 connected to the keyboard switches 44 through a 25-conductor shielded cable 105, and to the data acquisition card 70 through a 68-conductor shielded cable 106. The interface 100 provides, for each keyboard switch 44, an LED 101 connected in series with a pull-up resistor 102 and an inverter 103 between a 5-volt power source and ground. With this arrangement, the LED 101 turns ON when the corresponding keyboard switch 44 is pressed and a HIGH signal is supplied to the data acquisition card 70. The LED 101 provides a visual indication that the digital signal conditioning circuit 61 and the keyboard switches 44 are working properly.

Figure 7:
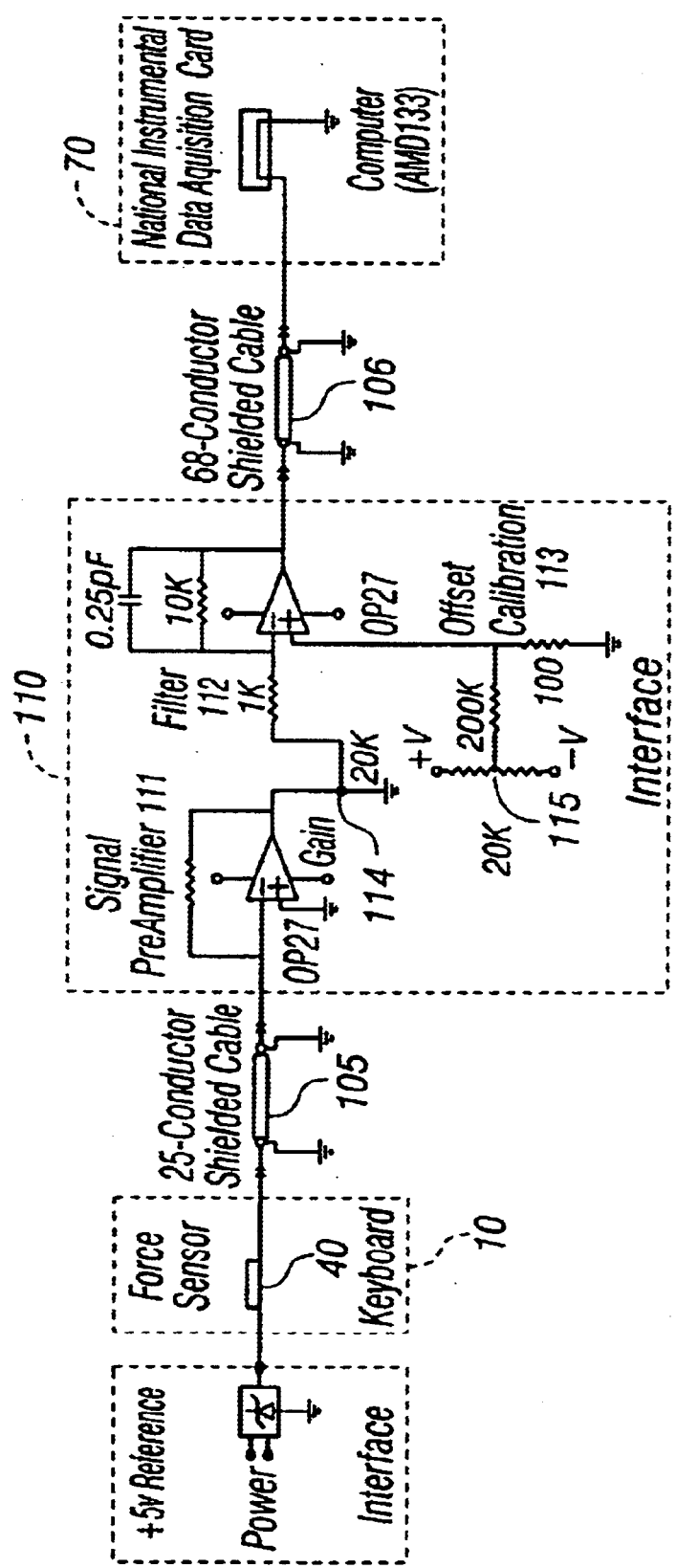
FIG. 7 is a schematic illustration of an analog signal processing circuit for the force sensors arranged on the ergonomic keyboard of FIG. 3A.

Referring to FIG. 7, the analog signal conditioning circuit 62 for the flexi-force sensors 40 comprises an interface 110 connected to the sensors 40 through a 25-conductor shielded cable 105 and to the data acquisition card 70 through a 68-conductor shielded cable 106. The interface 110 includes a signal pre-amplifier 111, a filter 112, and an offset calibrator 113. The signal pre-amplifier 111 and the filter 112 employ a low noise operational amplifier (not shown) in a single-ended arrangement to produce an analog output based on the force applied to the force sensor 40. It also includes a 10-turn potentiometer 114 for signal-gain control to provide a better resolution during the gain-calibration procedures. The output filter 112 includes an operational amplifier, a resistor and a capacitor that are configured to block out high frequency signal components. The cutoff frequency may vary, but can be set to 63 MHz. The offset calibrator 113 includes a 10-turn potentiometer 115 and introduces an offset or bias to the amplified and filtered flexi-force sensor output signal in accordance with the setting of the 10-turn potentiometer 115.

Figure 8B:
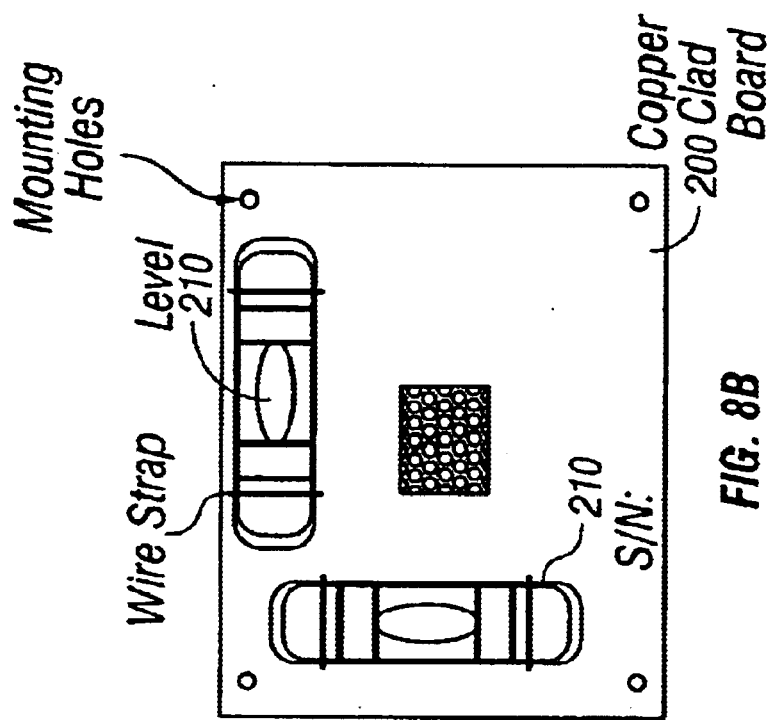
FIG. 8 illustrates side (8A) and top (8B) views of a calibrator used for the finger force sensors.
Figure 8A:
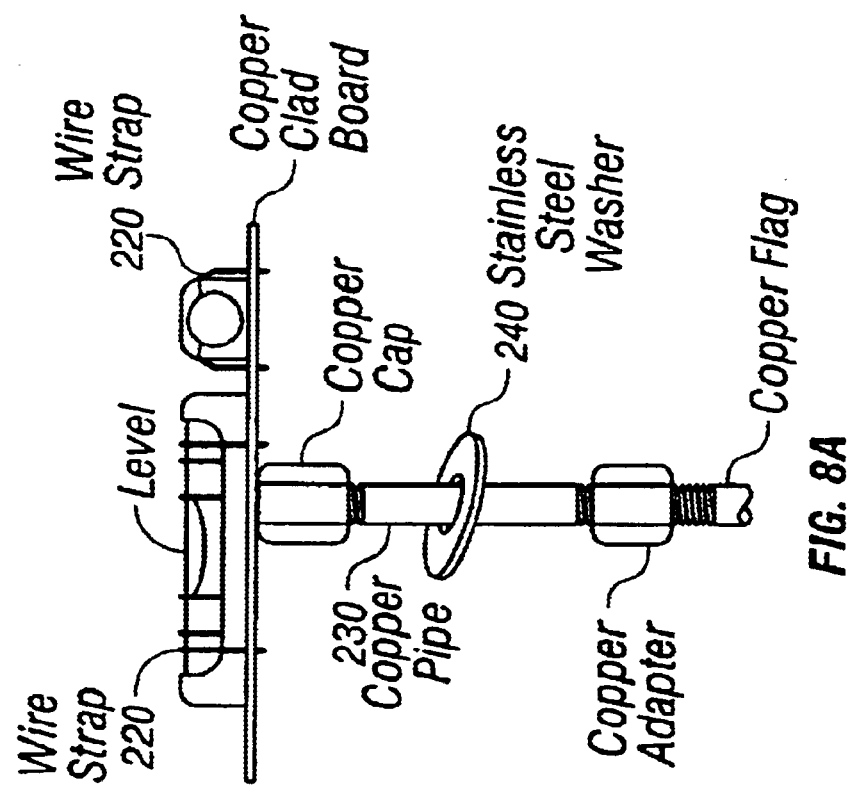

FIG. 8 is a top view (8A) and a side view (8B) of a calibrator used for the force sensors. Each key is calibrated separately after the force sensor has been fixed firmly in its place. Various known forces are applied to the force sensor and the electrical output signals are measured. The relationship between the input force magnitude and the output signal magnitude obtained in this manner is used to quantify the applied force in terms of Newtons relative to voltage output.

The calibrator illustrated in FIG. 8 includes a copper clad board 200, levels 210 secured to the copper clad board 200 with wire straps 220, a copper pipe 230 that extends below the copper clad board 200, and a stainless steel washer 240 mounted on the outer circumference of the copper pipe 230. The operation of the calibrator is as follows.

First, using micro-manipulators that encircle the stainless steel washer 240, the copper pipe 230 is placed over the key which has the flex-force sensor. Second, the micro-manipulators that support the calibration platform (mainly the copper clad board 200) are positioned until the levels 210 indicate that the platform is level. Third, weights are placed incrementally on the platform. During this step, the levels, as well as the electronic output, are monitored. Fourth, additional weights are continued to be placed on the platform incrementally until the flexi-force sensor is saturated at a weight that matches the manufacturer's reported force level, e.g., 4 lbs. Fifth, the weights are removed incrementally. Preferably, these steps are repeated two additional times, and throughout this process, the weights placed on the platform and the electrical signal output are recorded.

Testing with the FMS is carried out in the following manner. The apparatus is set to sample signals at a given frequency. For example, setting the apparatus to take samples at a frequency of 1000/sec. allows for the accurate capture of EMG signals simultaneously with signals representing force measurements. Lower frequencies can be used when EMG signals are not being measured.

Figure 9:
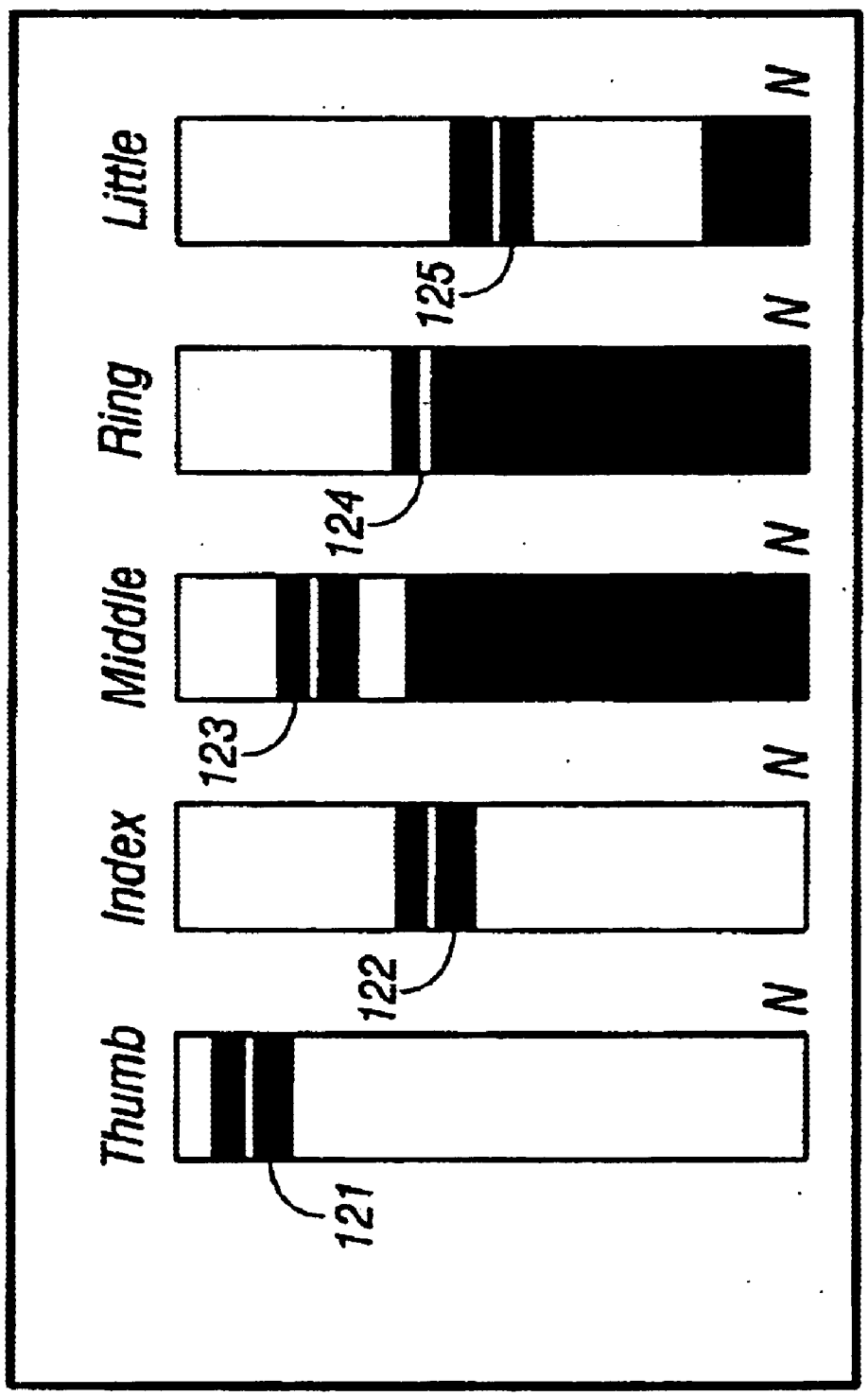
FIG. 9 is a sample display that provides visual feedback of the forces generated by the subject while the subject is being monitored for fatigue with the keyboard of FIG. 3A.

The subject is seated in front of the data display 90 referred to in FIG. 5, and further depicted in FIG. 9, which depicts a sample screen that is displayed to the subject during testing to provide feedback to the subject regarding finger force levels. To begin testing, the subject's hand is placed on the ergonomic keyboard 10 depicted in FIG. 4. To determine the target force levels, the subject is first asked to generate the maximum force by way of an isometric contraction of the fingers. The fingers are contracted during this step either all at once or separately. The maximum force levels are used to define the target force level for each finger during the test. The "target force level" is the amount of force the subject is required to produce while striking the keys. This target force level can be defined as thirty percent of the maximum force level, but other percentages may be used as well. The target force levels for each of the fingers are indicated in FIG. 9 as "bubbles" 121–125 in the display.

After setting the target force level, the subject is prompted to depress each key repetitively in a particular rhythm established either by the subject or externally for a period of time. The subject can be instructed to depress the keys either individually with the same finger or in sequence by different fingers. The onset of fatigue can be correlated to a drop in finger force level below the target force level. For example, a 20% drop can be defined as the point of fatigue. It is to be understood, however, that the 20% value is only exemplary, and this value may be defined to be larger or smaller.

In an alternative embodiment, a metronome may be provided. The metronome aids the subject in depressing the keys according to a predetermined rhythm. The metronome also allows for force measuring of different subjects under consistent test conditions, and/or force measuring of the same subject at different times under consistent test conditions.

Figure 10A:
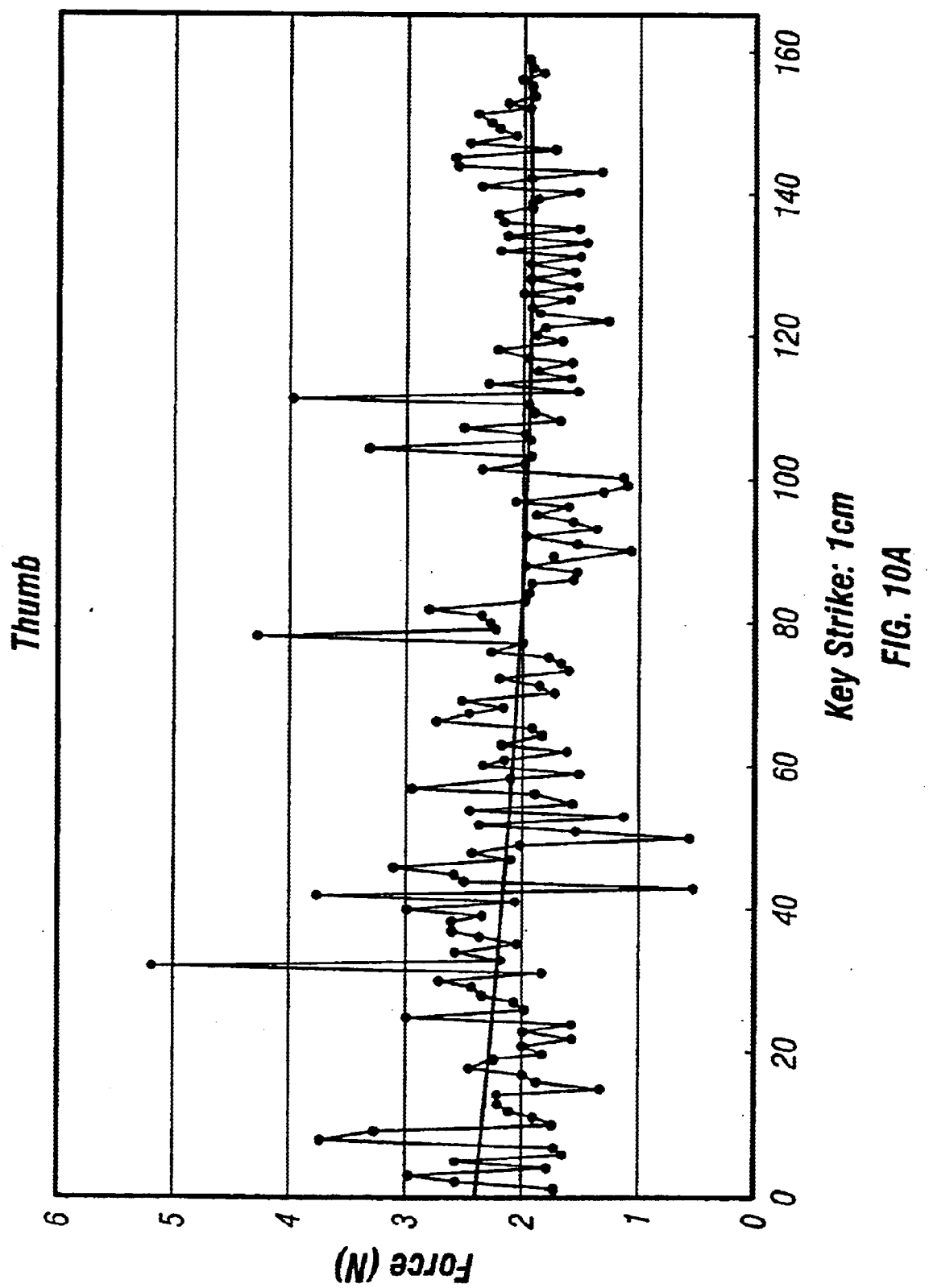
FIGS. 10A–10E are sample force production profiles for each of the fingers on a test subject's hand as follows: 10A-thumb, 10B-index finger, 10C-middle finger, 10D-ring finger, and 10E-little finger.
Figure 10B:
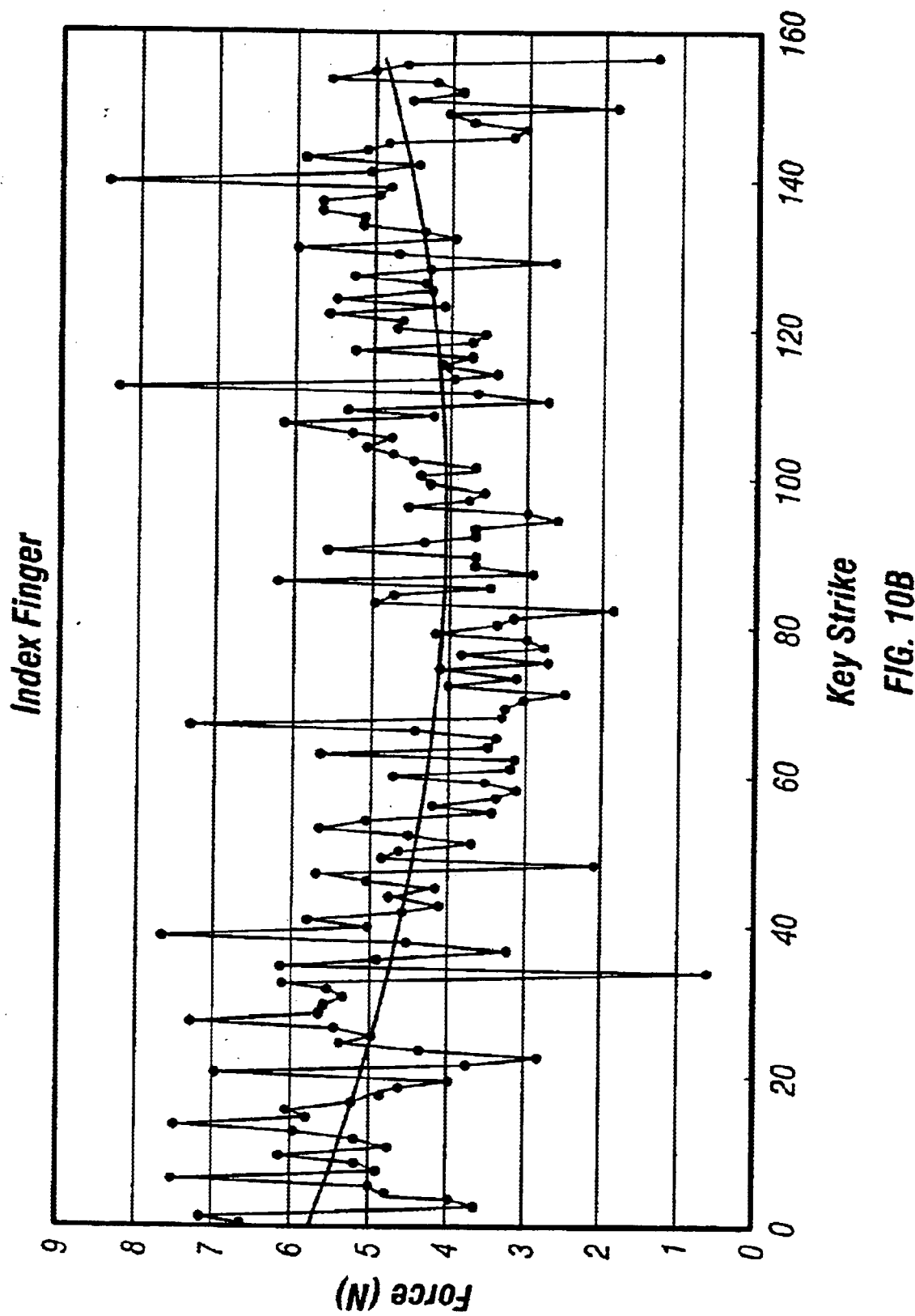
Figure 10C:
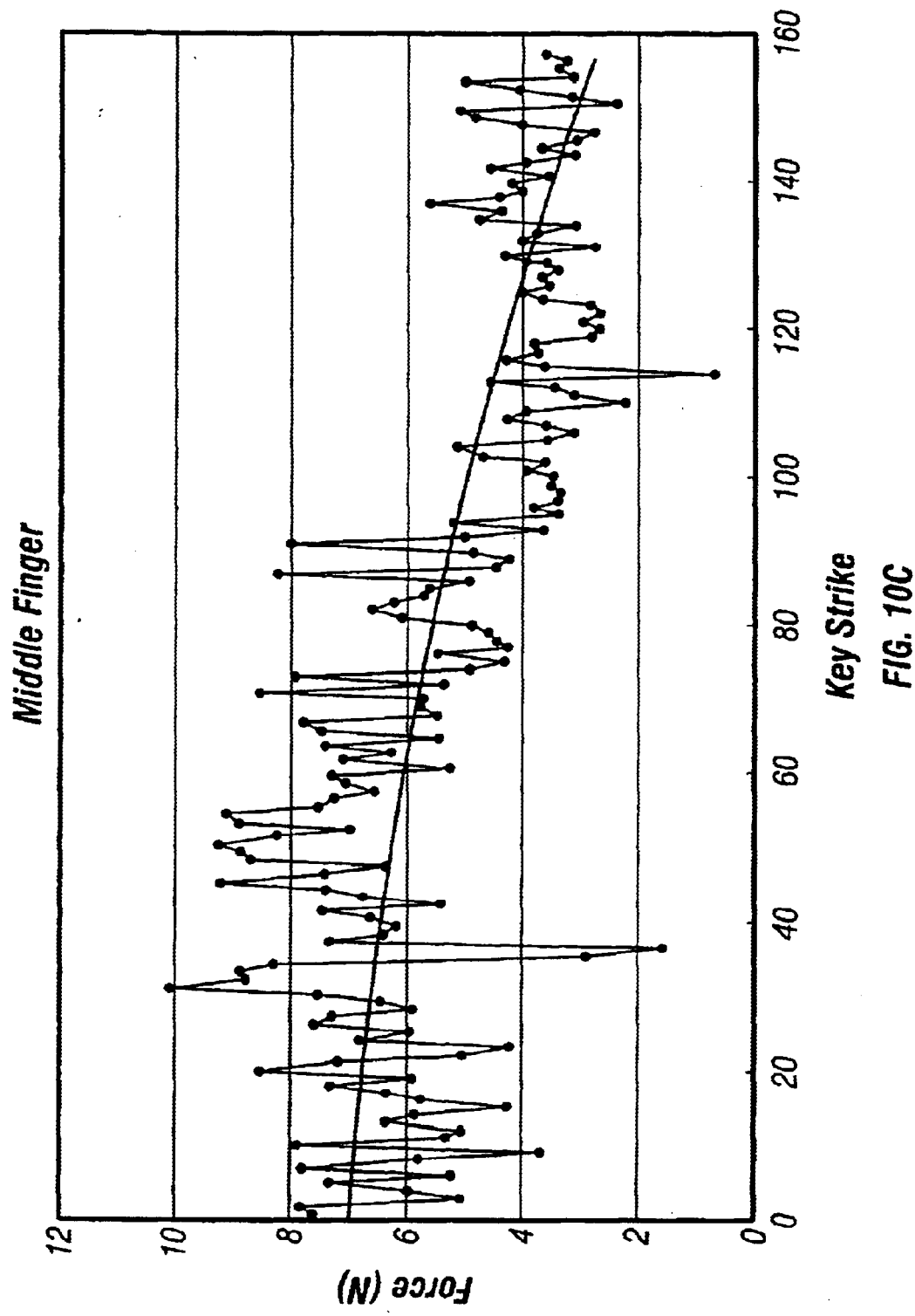
Figure 10D:
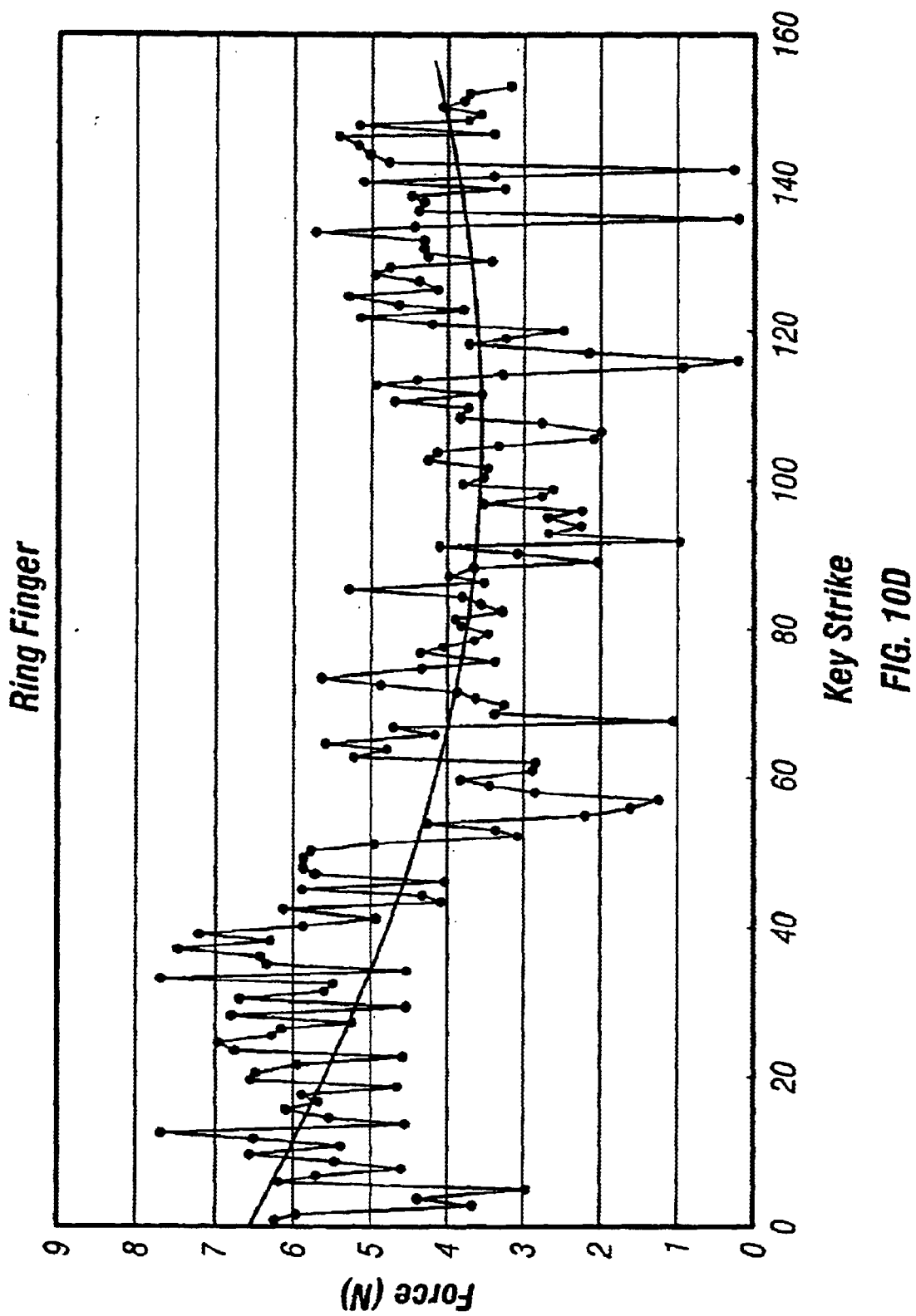
Figure 10E:
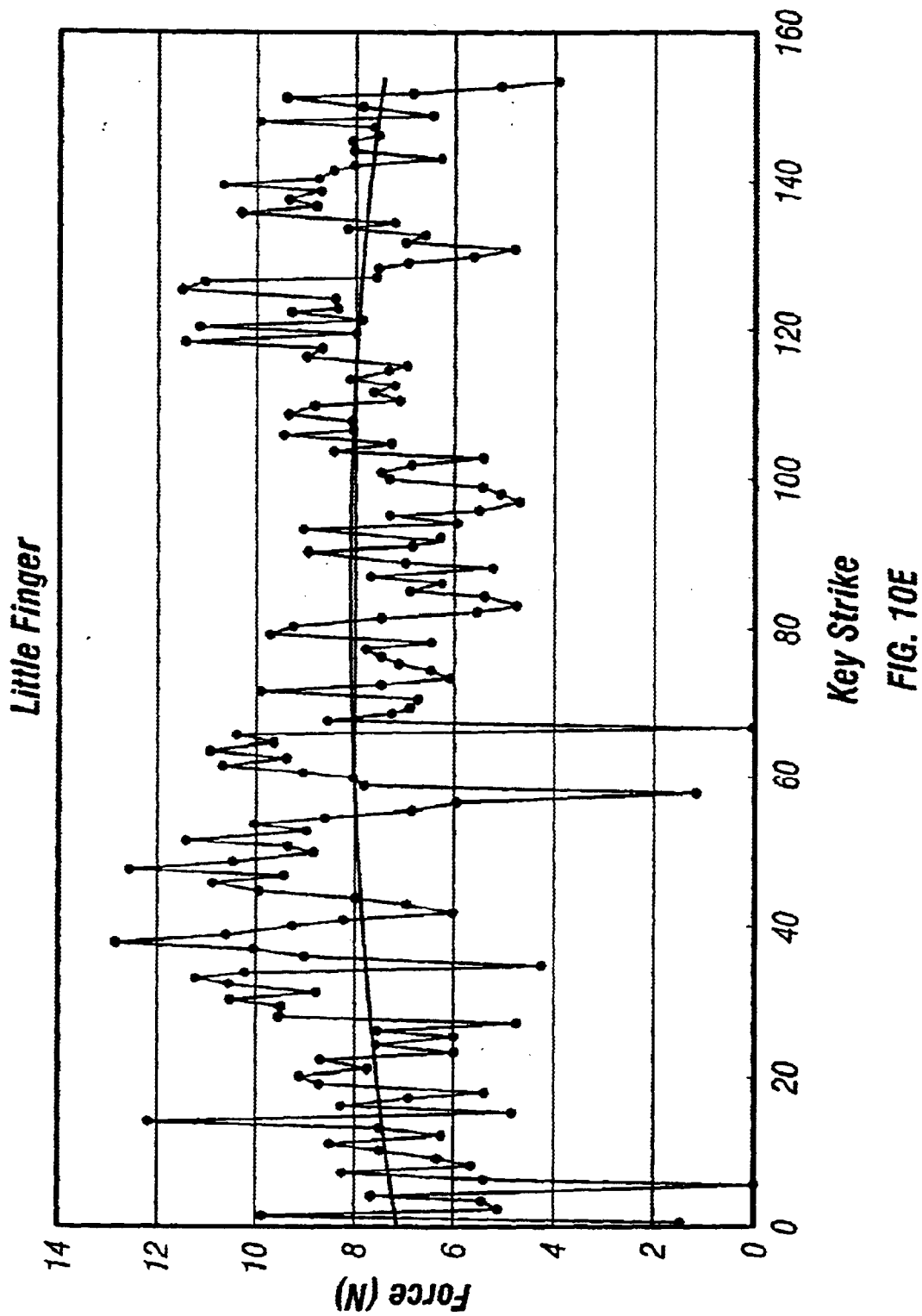

After the evaluation session, an exponential curve is fitted to the cumulative data of each peak force value recorded over time, and a drop in amplitude is monitored. FIGS. 10A–10E are sample finger force profiles, calibrated in terms of Newtons. FIG. 10A is a force production profile for the thumb. FIG. 10B is a force production profile for the index finger. FIG. 10C is a force production profile for the middle finger. FIG. 10D is a force production profile for the ring finger. FIG. 10E is a force production profile for the little finger. In each of FIGS. 10A–10E, the solid line running across the center of the force production profile is the "trend line" (i.e. the exponential curve based on the measurement of amplitude changes). As shown, not all fingers become fatigued at the same rate. In fact, as shown in FIG. 10B, after the onset of fatigue (drop in trend line) other muscles are recruited to compensate for the fatigue (raise in trend line). When the drop in amplitude is greater than a predetermined percentage, e.g., 20%, fatigue is considered to have developed. In addition to amplitude changes, each force production profile can also be evaluated for other changes to the force waveform, such as the upward and downward slopes. Furthermore, rather than evaluating the force production profiles separately for each finger, the collective force production profile of all of the fingers may be evaluated in a similar manner.

Figure 11:
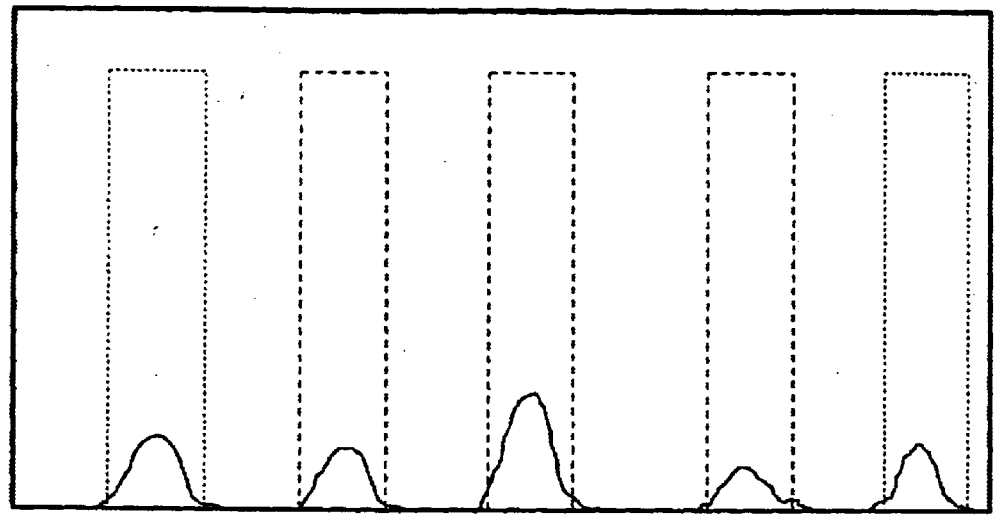
FIG. 11 graphically depicts the force production profile (solid line) superimposed with the force effect profile (dotted apparatus line) generated using the depicted in FIG. 8.

Software packages are commercially available that can be used to analyze various aspects of the force profiles, including the number of key strikes, the time of each key strike depression and release, the width of the force profiles, the amplitude or height of the force production profile, and the area under the force production profile. Analysis of the force effect profile include looking for a trend towards an increase in the time period between depression and release (i.e. the frequency of force effect events which are depicted in FIG. 11 as rectangular signal waves). If the repetitive motion is not being timed, such as with a metronome, a decrease in the frequency of the repetitive motion may result in an increase in the time it takes to perform each motion. In addition, when the subject is requested to perform sequential motor movements when timing is closely regulated, such as sequentially depressing keys in time with a metronome, a trend towards an overlap in depression and release from one finger to the next is another indication of fatigue.

The software may also record the data submitted by the subject, such as gender, previous complaints, work history, age, and other factors that may affect the person's finger force profile. Graphical representations of the force production profile include force peak, width, and area for all fingers. For example, FIG. 11 graphically represents the force effect profile generated from the depression and release of the keys (dotted line) along with the force production profile generated from the force waveform (solid line).

Figure 12:
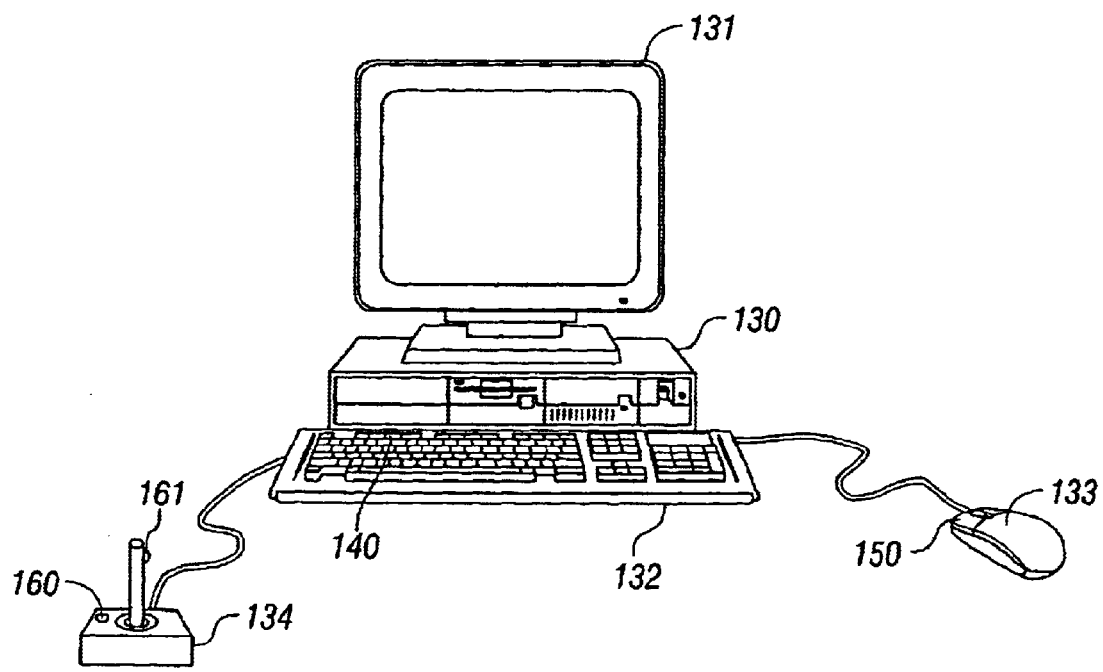
FIG. 12 is an illustration of a force measuring system incorporated into a personal computer system that includes a mouse and joystick.

FIG. 12 is an illustration of a FMS which is interfaced with a personal computer system that includes a case 130, a display 131, input devices which may include a keyboard 132, a mouse 133, and a joystick 134. The signal conditioning unit and the data acquisition card of the FMS are housed inside the case 130 and are controlled b y the microprocessor of the personal computer system which is also housed inside the case 130.

In an alternative embodiment, rather than the force measuring system being directly connected to the computer with which the signal processing and data analysis will occur, the FMS may be adapted to be capable of sending force profile signals via wireless transmission to a computer at a remote location.

In one embodiment, one or more of the keys of the keyboard 132 may include a flexi-force sensor which transmits signal proportional to the force applied to the corresponding key to the signal conditioning unit housed in the case 130. Alternatively, one or both of the mouse buttons 150 may include such a flexi-force sensor. An additional sensor may be provided on the mouse to measure the forces generated by the palm of the hand as the user is holding the mouse. The signals from this palm force sensor may be used as another measurement of fatigue, since as the person becomes fatigued using the fingers, he or she will put more force on the palm force sensor.

In yet another embodiment, a joystick 134 with a fire button 160 and/or a fire trigger 161 may be used as the input device. Either or both of the fire button 160 and the fire trigger 161 may include a force sensor. An additional sensor may also be provided on the joystick shaft to measure the forces generated by the palm of the hand as the user is holding the joystick shaft. The signals from this palm force sensor can be used as another measurement of fatigue, since as the person becomes fatigued activating the fire trigger 161, he or she will put more force on the palm force sensor.

Figure 13:
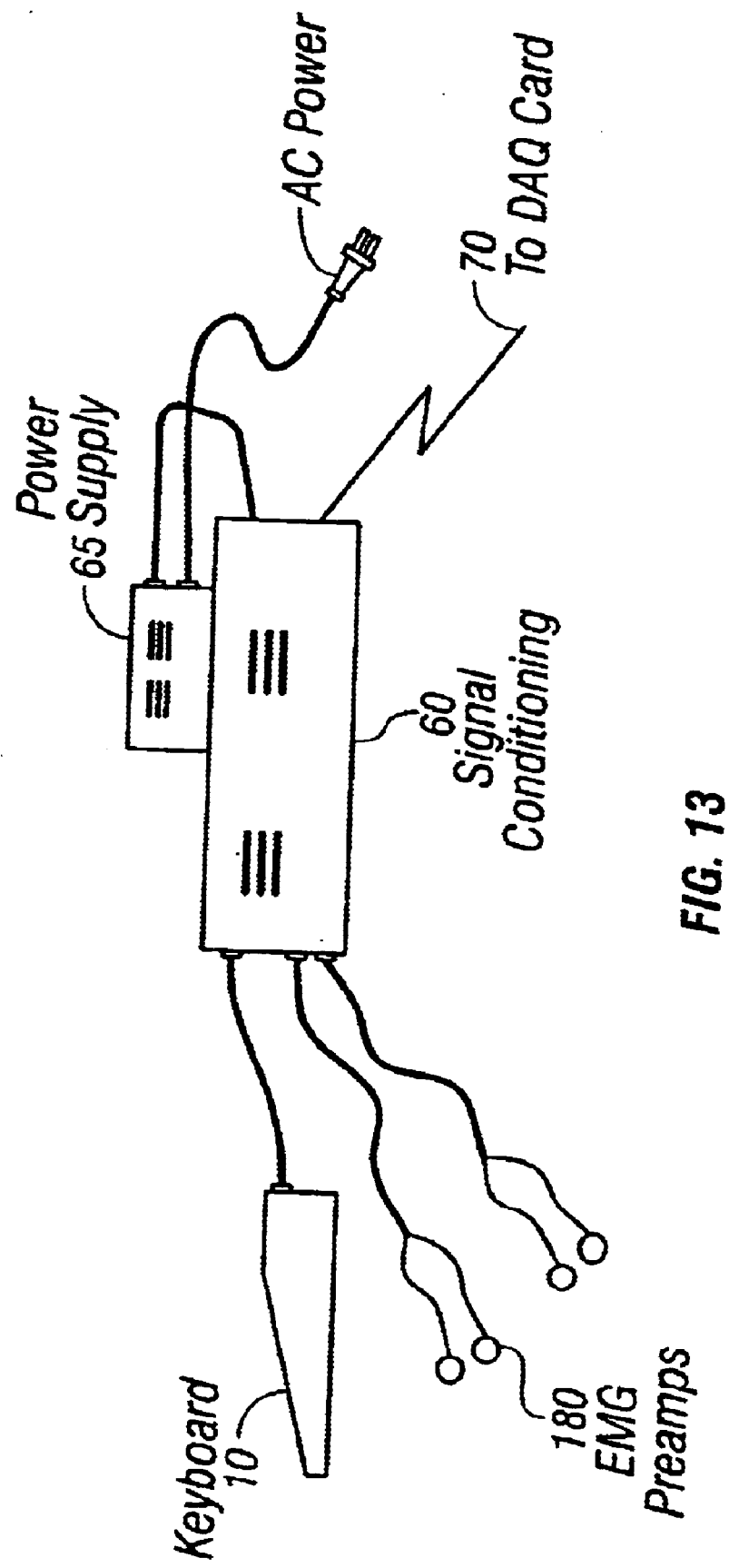
FIG. 13 is an illustration of a force measuring system which also includes means for measuring EMG.

FIG. 13 is an illustration of the FMS shown in FIG. 3B, which also includes a plurality of EMG preamps 180 for attachment to the test subject's muscles that generate the finger forces, namely the forearm muscles. The EMG preamps are connected to the signal conditioning unit 60 by a plurality of cables, and the EMG signals that are collected are correlated with the force profiles. The circuit for producing the EMG signals is considered to be well known in the art and is described, for example, in Eskelinen, U.S. Pat. No. 5,349,963. However, to correlate force data and EMG signal, it is preferred to measure force at a level of 1 kHz.

An increase in the slope of EMG signal amplitude or a decrease in the median frequency of the EMG signal are considered to be objective signs of fatigue, and these objective signs may be correlated with various characteristics of the force profile that are measured using the FMS, including but not limited to: slope, intercept, start and end of the signal, percentage change between the start and end of the signal, the total time of the repetitive motion and the ratio between the percentage change divided by the total time. For example, the EMG data may be superimposed with the force profile and the key depression and release. This allows one to visualize the electrical activity that generates the force that causes the key depression and release simultaneously with the force measurement.

The FMS of the present invention can also be incorporated into any mechanical de vice that interfaces with a computer. There are several specific additional applications that are contemplated. The first is in the area of affective computing. Presently, systems are being developed to monitor, inter alia, heart rate, blood pressure and sweat rate while persons operate a computer to get an indirect reflection of their emotional state. Affective computing assumes that the way a person hits a key may not only reflect physiological forces but also an emotional component. Thus, the amount of force being generated may be influenced by emotional factors. Regardless, the force profile may provide important feedback to the subject (or other person, such as a prospective or current employer) regarding the subject's overall state of wellness.

The FMS may also be used in the evaluation of strengthening devices. As CTS and other forms of RSI increase, it is expected that the market for various forms of finger strengthening devices will increase. The present invention may be used in conjunction with such devices to monitor the characteristics of force produced by a body part while using such a strengthening device.

The FMS may also be incorporated into any system in which force is repetitively being produced to give feedback to the subject to decrease the amount of force that they are producing. This feedback would act to minimize RSI caused by the generation of excessive force after the onset of fatigue.

The FMS may be also used to evaluate the efficacy of various clinical interventions. Measurements of the force profile before and after clinical treatment for CTS or any other RSI may be an objective measurement of the efficacy of clinical interventions. In addition, the FMS may be used to quantify various motor problems in subjects suffering from various diseases ranging from schizophrenia to Parkinson's disease. In some cases, finger tapping is a clinical assessment of motor problems. In addition, in medical fields such as physical therapy or occupational therapy, mechanical devices are used to evaluate and/or increase the strength or dexterity of the subject. The FMS is not limited to keyboards, joysticks or a mouse but can be used in conjunction with any mechanical system that involves repetitive motor movements such as the fingers twisting a boll or putting objects into specific locations.

In addition, the FMS may be used as an important pre-employment tool. Evaluating a person's force profile as described herein may be used before employment, and would serve as a benchmark in the event that the employee subsequently develops RSI or alleges that they do.

Another application for the systems of the present invention is its use in assisting an individual playing sports to make changes to optimize the outcome of their motor movements. For example, if a FMS is incorporated into a golf club handle, a golfer may be alerted when the club is being held too tight in order to learn when to loosen her grip.

It will also be understood that the present invention may be used in situations where monitoring fatigue per se is not necessary. For example, the FMS may be interfaced with a computer-driven game, and the force profiles may be used as input to the game to modify the scenario, the rate of presentation for the player, or any other game parameter. For example, force sensors may be included in buttons of the game controllers, and data from the force sensors can be processed by the computer to evaluate how the person is playing in terms of the characteristics (e.g. speed, amount, decline, etc.) of force that they apply to certain buttons during the game. The computer can then modify the game in any manner, such as making it more challenging. In addition, EMG data (or other data representative of physical or physiochemical manifestations, such as electrocardiograms, electroencephalograms and/or galvanic skin responses) may be monitored as well, and this activity data may be used by the computer alone or in conjunction with the force data to modify the game. To carry out the above functions, the computer may also be programmed to have some form of software interface such as a neural network configuration or other program that monitors the force profile of the player(s) and modifies the game.

Indeed, the FMS when correlated with EMG signals may be used to further evaluate the force produced and the onset of fatigue during any repetitive motions. For example, the FMS can be interfaced with any piece of exercise equipment, such as a bicycle, or any isotonic or isokinetic strengthening system, to provide information about force and fatigue.

Other applications include the following: measuring the change in force one generates when standing on a mat as an indication that the person is fatigued and should sit down; measuring the change of force applied by the wrist to a wrist pad or by the forearm to an armchair when typing as an indicator of fatigue; measuring the change of force while using power tools for industrial safety in setting limits on the time period that the tools can be used to prevent fatigue-related accidents; and biometric applications involving use of the force profiles for identifying individuals or classes of individuals with similar profiles. The latter can be used in conjunction with other physiological signatures or biometrics, such as voice recognition, for "fingerprinting" an individual.

In addition to the aforementioned applications, the present invention can be adopted to provide "biofeedback" information to the subject by displaying either or both type(s) of force profile(s) on a video monitor, which the subject would then be expected to react to by changing their application of force to the force sensing apparatus.

Numerous modifications may be made to the foregoing invention without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

We claim:

1. A method for measuring force produced by at least one body part of a subject performing repetitive motions, said motions including applying force to a force sensing member connected to a force measuring apparatus, said method comprising the steps of:

a) measuring a signal as a function of force produced by the body part during performance of the repetitive motions;

b) measuring a signal as a function of force effects on the force sensing member during performance of the repetitive motions;

c) converting the signal from step a) to a force production profile; and d) converting the signal from step b) to a force effect profile.

2. The method according to claim 1, wherein step a) further comprises generating measurable signals in proportion to the forces.

3. The method according to claim 2, wherein step c) further comprises converting the signal into a sequence of discrete force production data representative of the forces generated by the body part.

4. The method according to claim 1, further comprising the step of measuring EMG signals from one or more muscles of the subject.

5. The method according to claim 4, further comprising the step evaluating the EMG signals for fatigue.

6. The method according to claim 1, wherein the body part is a finger, said finger being part of a hand, and wherein the repetitive motions are repeatedly pressing keys with fingers.

7. The method according to claim 6, wherein step a) further comprises generating signals in proportion to the forces produced by the fingers pressing the keys.

8. The method according to claim 7, wherein step c) further comprises converting the signals into discrete force production data representative of the forces generated by the finger.

9. The method according to claim 6, wherein the hand further comprises a hand base.

10. The method according to claim 8, further comprising the step of measuring a baseline force output for each of the fingers.

11. The method of claim 10, further comprising the step of normalizing the discrete force production data with the baseline force output to produce normalized force production data representative of the forces generated by the fingers.

12. The method according to claim 11, further comprising the step of calculating a rate of amplitude change from the normalized force-production data.

13. The method according to claim 12, further comprising the step of converting the rate of amplitude change into a value representative of fatigue.

14. The method according to claim 9, further comprising the step of measuring signal characteristic of force produced by the hand base as the keys are repeatedly pressed with the fingers.

15. The method according to claim 14, wherein step a) further comprises generating a first set of signals in proportion to the forces produced by the hand base and a second set of signals in proportion to the forces produced by the fingers.

16. The method according to claim 15, wherein step d) further comprises converting the first set of signals into a first set of discrete force data representative of the forces generated by the hand base and converting the second set of signals into a second set of discrete force data representative of the forces generated by the fingers.

17. The method according to claim 16, further comprising the steps of calculating a first rate of amplitude change from the first set of discrete force data and a second rate of amplitude change from the second set of force data.

18. The method according to claim 17, further comprising the step of converting the first rate of amplitude change, the second rate of amplitude change or the relationship between the first rate of amplitude change and the second rate of amplitude change into a value representative of fatigue.

19. The method according to claim 1, wherein step d) further comprises determining a force effect event frequency from the force effect profile.

20. A force sensing member adapted for use in a force measuring apparatus for measuring force produced by at least one body part of a person performing repetitive motions, said force sensing member comprising:
   a) a force sensor functionally associated with the force sensing member that generates a signal characteristic of force produced by the body part and transmitted to the force sensing member during performance of the repetitive motions; and
   b) a switch sensor functionally associated with the force sensing member that generates a signal when depression and release of the force sensing member occurs during performance of the repetitive motions.

21. A force measuring apparatus comprising at least one force sensing member according to claim 20 and a housing.

22. A force measuring system comprising the force measuring apparatus of claim 21 and a computer, wherein said computer further comprises a processor, and wherein said processor converts: the signal from the force sensor to a force production profile; and the signal from the switch sensor into a force effect profile.

23. The force measuring apparatus according to claim 21 further comprising a keyboard having a plurality of keys, wherein the force sensor and switch sensor are functionally associated with at least one key.

24. The force measuring apparatus according to claim 21 further comprising a computer mouse having a mouse button, wherein the force sensor and switch sensor are functionally associated with the mouse button.

25. The force measuring apparatus according to claim 21 further comprising a joystick having a firing button, wherein the force sensor and switch sensor are functionally associated with the firing button.

26. The force measuring system according to claim 22, wherein said computer further comprises an output device for displaying the force production profile and the force effect profile.

27. A computer game system adapted for measuring force produced by at least one body part of a person performing repetitive motion while playing the computer game, wherein said system comprises a force sensing member further comprising:
   a) a force sensor functionally associated with the force sensing member that generates a signal as a function of force produced by the body part and transmitted to the force sensing member during play of the game; and
   b) a switch sensor functionally associated with the force sensing member that generates a signal when depression and release of the force sensing member occurs during play of the game.

28. The computer game system according to claim 27 further comprising a processor, wherein said processor is programmed to
   a) receive signal from the force sensor and convert the signal to a force production profile; and
   b) receive signal from the switch sensor and convert the signal to a force effect profile.

* * * * *